United States Patent [19]

Wolfram et al.

[11] 4,416,297

[45] Nov. 22, 1983

[54] HAIR WAVING OR STRAIGHTENING PROCESS AND PRODUCT

[75] Inventors: Leszek J. Wolfram, Stamford; David Cohen, Milford; Norman N. Tehrani, Stamford, all of Conn.

[73] Assignee: Clairol Incorporated, New York, N.Y.

[21] Appl. No.: 292,452

[22] Filed: Aug. 13, 1981

Related U.S. Application Data

[63] Continuation-in-part of Ser. No. 114,479, Jan. 23, 1980, abandoned.

[51] Int. Cl.³ .............................................. A45D 7/04
[52] U.S. Cl. ........................................ 132/7; 424/70; 424/71
[58] Field of Search .......... 132/7; 424/70, 71, DIG. 2

[56] References Cited

U.S. PATENT DOCUMENTS 3,964,499  6/1976  Wajaroff et al. ..................... 132/7
4,175,572  11/1979  Hsuing et al. ......................... 132/7

*Primary Examiner*—C. Fred Rosenbaum
*Assistant Examiner*—Sherri Vinyard
*Attorney, Agent, or Firm*—Gabriel P. Katona

[57] ABSTRACT

A process for waving or straightening hair in which an anionic surfactant is added to the hair reducing solution and the hair is treated either during a prewetting step or during neutralization, or both with a cationic polymer product which forms a substantially water insoluble complex with the anionic surfactant in the presence of hair.

25 Claims, No Drawings

HAIR WAVING OR STRAIGHTENING PROCESS AND PRODUCT

This is a continuation-in-part of application for U.S. Letters Patent Ser. No. 114,479, filed on Jan. 23, 1980 abandoned.

This invention relates to a hair waving or straightening process which simultaneously conditions the hair to prevent tangling and to leave it in an easily combable condition which persists through several shampoos.

Cold waving or permanent waving of hair and treatments for straightening hair are essentially similar in that the hair is first treated with an agent which softens or cleaves the disulfide bonds of keratin to allow a reshaping of the hair, whether it be to form waves or to straighten overly curly hair. This is referred to as "reducing". After a usual intermediate rinse, the hair that was softened by the preceding treatment, is set into its new shape by a subsequent step which is usually referred to as "neutralization" which neutralizes the effect of the reducing agent by reestablishing the cleaved linkages. A considerable number of processes and materials useful in these processes are well known for the waving or straightening of hair. The present invention generally relates to an improvement of all such processes.

Exposure to such waving or straightening processes is almost invariably accompanied by a tangling of the hair and a deterioration of the tactile properties and difficulty in subsequent combing. This can often be exacerbated in the case of hair which, prior to waving or straightening, had been exposed to bleaching, coloring or prolonged weathering. Conventionally, hair is treated to ameliorate the situation, with various conditioning agents, including emulsions of mineral oil, lanolin, alkyl-dimethyl benzyl halides, quaternary ammonium compounds and the like. Conditioning agents of this type are usually incorporated in the neutralizing step of the waving or straightening process. While these conditioning compounds improve the feel of hair and allow for easier combing, their beneficial effects are only transitory and are entirely lost when the hair is subsequently shampooed.

SHORT DESCRIPTION OF THE INVENTION

It has now been found that durable conditioning of hair during waving or straightening operations can be obtained by a process wherein the composition employed in softening the hair such as by cleaving the disulfide links in keratin, contains an anionic surfactant or an amphoteric surfactant under a pH to make it at least partly anionic, and the hair is also contacted with a composition containing a cationic polymer product (as defined hereafter) in solution, the contacting being carried out at a time other than during the reduction, the softening step or cleaving of the disulfide links in the hair. The composition to be used in accordance with the present invention can be suitably sold in a package which contains a plurality of containers suitably along with instructions on how to employ them.

The present invention is based on the discovery that in conjunction with a waving or straightening composition, when a cationic polymer product is contacted with an anionic surfactant in situ on the hair an insoluble complex is formed and the positive charges form a strong bond with the negative charges of the hair. Thus the complex, which when formed in the presence of hair was found surprisingly to have excellent conditioning characteristics, becomes firmly bonded to the hair and survives a variety and a number of subsequent treatments to the hair and remains bonded to it and thus continues to condition it in a durable fashion.

DESCRIPTION OF THE PRIOR ART

Quaternary ammonium compounds have been widely employed for the conditioning of hair. It is also known e.g. from U.S. Pat. No. 4,061,150 to follow the treatment by a non-polymeric cationic conditioner, with a shampooing with an anionic shampoo. This patent emphasizes that it requires small, rapidly diffusing quaternary amine molecules in contradistinction from polymeric cationic substances which cannot be used in accordance with the patent. Although the patent mentions that the resulting deep penetration of the treatment medium into the hair through cracks and crevices in the hair, remains there through a number of subsequent shampoos "adding body and suppleness to the hair strand", we know from experience that when the teachings of this patent are followed no durable conditioning, as measured by combability, can be obtained thereby.

The use of cationic polymer products on hair, in general, is of relatively recent origin. U.S. Pat. No. 3,912,808 discloses the use of a particular cationic homopolymer, dimethyldiallylammonium chloride, in a waving or straightening composition wherein a specified polymer is incorporated into the composition which contains the disulfide bond-cleaving, so called "reducing agent". The patent makes it quite clear that the polymer is incorporated into the composition containing the reducing agent, instead of being used in the form of separate solutions separately applied. The patent clearly evidences the lack of recognition which was made by the present invention that the reaction product between the cationic polymer and an anionic detergent form in situ a highly useful durable conditioning complex on the hair. This conclusion is further supported by the fact that the patent also teaches the use of a copolymer of the specific polymer with acrylamide and, as will become evident later, such copolymer is not suitable to be employed in accordance with our invention.

Moreover the patent also discloses in very general terms the use of the specific cationic polymer also in areas other than waving or straightening, to wit in hair coloring and hair bleaching compositions. In connection with the latter disclosed but unclaimed uses, a surface active agent can be employed for the purpose of maintaining the composition homogeneous, i.e., in a single phase. The patent goes on to say that in hair coloring and bleaching compositions that contain an anionic surface active agent, the specific cationic polymer remains effective despite the fact that ionic intereaction in the container would be expected to lead to the formation of an inactive and insoluble catan wax. Furthermore, our invention employs the surfactant in a hair waving or hair straightening process, and not in dyeing, to achieve the surprisingly beneficial durable conditioning effect.

The aforementioned U.S. Pat. No. 3,912,808 employs the specific cationic polymer in the composition which contains the reducing agent. In accordance with the present invention the reducing agent containing composition also contains the anionic surfactant, but it cannot contain the cationic polymer product. This is because if the anionic detergent and the cationic polymer product would be applied from the same composition, the insoluble complex would form in the composition before its application rather than in situ on the hair.

DETAILED DESCRIPTION

As already indicated, the present invention is equally applicable to all types of hair straightening processes which use a reducing composition to soften or cleave the disulfide bonds of keratin and a neutralizing composition to reestablish the cleaved linkages. Such processes employ various utensils for the winding of hair. Therefore, as used throughout the specification and the claims the term "waving or straightening rod" is intended to include in its definition other terms, such as curlers and rollers. Since the present invention is a supplement to any waving or straightening composition and process, there is no change intended to be made by this invention in the nature of the ingredients and their concentrations of present or future waving or straightening compositions, therefore, any reference below to reducing and neutralizing ingredients and concentrations, is merely illustrative but is not intended as limiting the present invention.

All types of reducing agents for waving or straightening can be employed in connection with the present process. Such agents generally soften the hair or otherwise cleave the disulfide bonds of the keratin in hair. Compounds customarily employed for this purpose include mercaptyl carboxylic acids, salts and esters. Typical examples are the most frequently used thioglycollic acid and also thiolactic acid. Also alkali salts of sulfurous acids, such as ammonium, sodium or potassium sulfites and bisulfites; cysteine; and guanidine or salts thereof, are all fairly frequently used, as is tris(hydroxyethyl phosphine). Therefore, as used throughout the specification and the claims, the term "reducing agent" is intended also to include, among others, such keratin cleaving and relaxing agents as are exemplified above. Usually 0.5% to about 20% of the reducing agent is employed.

In the neutralization step the disulfide keratin bonds are restored by exposure to an oxidizer such as a peroxide or a bromate, sometimes along with a reagent which will provide an exothermic reaction and associated heat. In some conventional compositions an increase of the pH during neutralization is the prime contributing factor in reestablishing the cleaved bonds. As used throughout the specification and the claims, the term "neutralizing agent" is intended to include all of the aforementioned types of compounds and treatments or any other means by which the action of the reducing agent on hair is neutralized.

The term "anionic surfactant" as used throughout the specification and the claims includes in its definition amphoteric surface active agents which become anionic under basic or near to basic conditions if the reducing and/or neutralizing of hair carried out in a composition having a basic or near to basic pH, i.e. above the $pk_a$ value of the amphoteric surfactant.

The cationic polymers that are useful in accordance with the present invention have at least one positively charged nitrogen or sulfur moiety in each periodically repeating unit. The functional quality of the water insoluble durable conditioning complex that is formed on, and adheres to, the hair, which will resist the effect of several subsequent shampooings, depends on a large extent on the characteristics of the particular cationic polymer that is employed. Therefore, it is conceivable that some of these cationic polymers which have at least one positively charged nitrogen or sulfur moiety in each periodically repeating unit, will not be as effective as others. This, in fact, was observed in the case of a number of cationic polymers.

A simple test was devised to determine the usefulness of materials for the conditioning of hair. The test and the associated simple instrumentation are described in an article by M. Garcia et al. in 27 Jnal. Soc. Cosmetic Chemists pp. 379-398 (September 1976) entitled "Combability Measurements on Human Hair", which is incorporated herein by reference thereto. The conditioning of hair is defined for purposes of the present invention as increasing the ease by wich a comb can be pulled through freshly washed hair. The term "durable conditioning" as is used throughout the specification and the claims means that after the application of the conditioning composition and the employment of a durable conditioning process, hair is easier to comb after at least three subsequent shampooings, than it is to comb when no conditioning was employed, even after a single shampoo. This defines what is meant by "durable" when we refer to "durable conditioning".

Whether hair is effectively conditioned or not can be simply determined by employing the measurement described in the above-mentioned article on combability measurements. A hair swatch is suspended from an Instron Tensile Tester having a load cell B which has a range of 0-2000 g. Other recording tensile testing instruments can also be used. An attachment is provided having a comb stand, a comb, clamps and the like. The exact character of the measuring device is not critical, since always relative values are determined in comparison to untreated hair. For determining the base line control value for a given hair, the hair swatch is soaked in water, then is combed out until detangled. Then the hair is dipped into water several times to cause controlled tangling. Then the hair is combed out and the force required to move the comb down through the hair swatch at constant speed is recorded. The effect of treatment on the hair swatch is determined by treating the swatch with an amount of treating agent, in the same manner as treatment is intended to be given to hair in actual use. The hair swatch is then relaxed by a 5 minute immersion in water and again the force is measured that is required to pull a comb through the swatch at constant speed. The difference is then calculated and will provide a measure of the conditioning efficacy of the treatment. In the case of the present invention the treatment is followed by 3 subsequent shampooings and, therefore, the measurement not only provides information about the conditioning efficacy of the treatment, but also about the durability of the effect.

In the case of the present invention in defining whether we can consider hair to have been conditioned, we cannot employ a scale of absolute force values as could be measured in accordance with the aforementioned article. This is because there are many different kinds of hair, all of which have different combability characteristics. Therefore, it is not usual that one variety of hair requires a force tenfold or more than the force required to comb another variety of hair that is in a stage of identical conditioning. Notwithstanding this fact, conditioners have been found generally, and especially in the case of the present invention, to improve the combability of all given varieties of hair that were tested.

Accordingly, we have assigned a subjective scale of 5 values to define the ease of combing, i.e. the degree of conditioning of hair, with the value 1 representing the combability of hair that was not conditioned at all. The value 2 represents a slightly perceptible increase in the ease of combing, but we do not consider hair to have been conditioned until it has a value of at least 3. If hair has a value of 3 after 3 shampooings, then we consider it to have been durably conditioned. It should be kept in mind that these five subjective ease-of-combing values are relative ones and are comparable to each other only when used in each case on the same kind of hair.

According to the arbitrary scale of 5 values, the value 1 was assigned to wet, untreated hair and 5 to the best conditioned value. In accordance with the force measurement that is required for combing, as described above, a maximum conditioning at level 5 would require about 1/10 of the force that is required for an untreated swatch of wet hair. If we consider a level 5 as representing a conditioning improvement of approximately 100%, then we can assign to levels 2, 3 and 4 an approximate improvement of 25%, 50% and 75%, respectively.

As used throughout the specification and the claims, the term "cationic polymer product" denotes a cationic polymer which has at least one positively charged nitrogen or sulfur moiety in each periodically repeating unit and which can form a substantially water insoluble complex when contacted with an ionic surfactant in the presence of hair, said complex durably conditioning the hair.

A number of different cationic polymers were tested to determine whether they satisfy the aforementioned requirements of a cationic polymer product. As a result of such testing it was determined that it is entirely unpredictable from the structural characteristics of a polymer whether or not it will perform as a cationic polymer product. For example, while quaternium-40, dimethyldiallylammonium chloride homopolymer sold by Merck & Co., INc. under the name Merquat-100, performed satisfactorily under the criteria for durable conditioning, as described above and is, therefore, a cationic polymer product, but its low molecular weight (5000) homolog is not, although even a lower molecular weight (3000) cationic polymer (polyquaternium-1) performed satisfactorily.

Other examples of cationic polymers which are not cationic polymer products because they did not perform satisfactorily are given by their official CTFA (Costmetic, Toiletry and Fragrance Association) names, where available, as contained in the CTFA Costmetic Ingredient Dictionary (1977 edition), followed by their trademark and source in parentheses. There are:

adipic acid/epoxypropyl diethylenetriamine copolymer (sold by Hercules Chemical Col. under the name Delsette 101);

adipic acid/dimethylaminohydroxypropyldiethylenetriamine copolymer (sold by Sandoz, Inc. under the name Cartaretin F-4);

poly [N-(3-dimethylamino)propyl]-N'-[3-(ethyleneoxyethylene dimethylamino)propyl] urea dichloride (sold under the name Mirapol A15 by Miranol Chemical Co., Inc.);

quaternium-23, a quaternary ammonium polymer formed by the reaction of dimethyl sulfate and a copolymer of vinyl pyrrolidone and dimethylaminoethylmethacrylate (sold by GAF Corporation under the name Gafquat 755N);

quaternium-19, a polymer of hydroxyethyl cellulose reacted with epichlorohydrin and then quaternized with trimethylamine (sold by Union Carbid Corp. under the name Polymer JR-400);

a quaternary ammonium derivative of a hydrolyzed collagen protein (sold by Croda, Inc. under the name of Crotein Q);

quaternium-39, a copolymer of acrylamide and beta-methacryloxyethyl trimethyl ammonium methosulfate (sold by Hercules Chemical Co. under the name Reten 205M);

aminoethylacrylate phosphate/acrylate copolymer (sold by National Starch Co. under the name Catrex); and quaternium-41 which is a copolymer of dimethyldiallylammonium chloride with acrylamide (sold by Merck & Co., under the name Merquat-550).

On the other hand, a number of other cationic polymers were found to perform well as ingredients of durable conditioning compositions in accordance with the present invention and they satisfy the definition of a cationic polymer product.

The cationic polymer products that were found so far are:

quaternium-40, already mentioned above as one good example. It is said to be constituted of repeated units of the moiety:

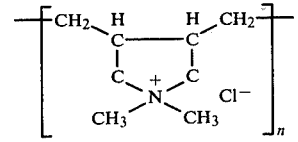

where n is a cardinal number proportional to the molecular weight of the polymer.

Other cationic polymers that were so far found to be cationic polymer products, are:

polyquaternium-1, a polymeric quaternized dimethylbutenylammonium chloride terminated with quaternized triethanolamine groups, sold by Onyx Chemical Co. under the name Onamer M, hereinafter referred to as "Onamer", and said to have the formula:

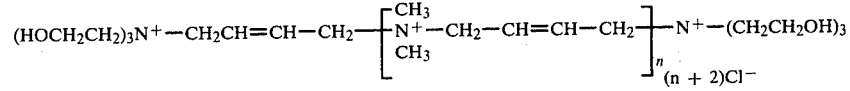

where n is a cardinal number which is proportional to molecular weight;

quaternized poly-4-vinyl pyridine, hereinafter referred to as "QPVP", which is believed to be constituted of repeated units of moiety:

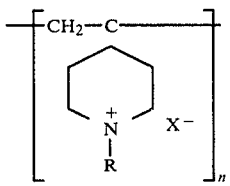

where n is a cardinal number which is proportional to molecular weight, R is a $C_1-C_{20}$ alkyl radical and X is a cosmetically acceptable anion such as a halide, sulfate or carboxylate, which can be made by quaternizing and then polymerizing vinylpyridine in a manner known per se;

poly (methacrylamidopropyltrimethylammonium chloride), hereinafter referred to as "Clairquat-1", which is made by polymerizing in a manner known per se the corresponding monomer sold by Texaco Chemicals under the name MAPTAC and which polymer is said to be constituted of repeating units of the moiety:

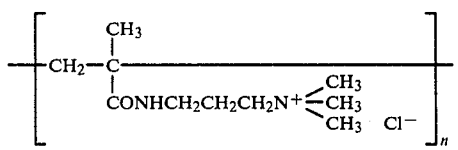

where n is a number which is proportional to molecular weight;

quaternized poly(vinylamine), hereinafter referred to as "QPVAMINE", which can be made by quaternizing and polymerizing vinylamine in a manner known per se, and which is believed to be constituted from repeating units of the moiety:

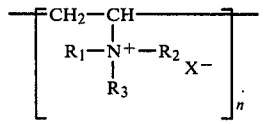

in which $R_1$, $R_2$, and $R_3$ are the same or different and represent $C_1-C_{20}$ alkyl groups, and X is a cosmetically acceptable anion such as a halide, sulfate, or carboxylate; and quaternized poly(ethyleneimine), hereinafter referred to as "QPEMINE", which can be prepared by quaternizing and polymerizing ethyleneimine in a manner known per se, and which is believed to be constituted from n repeating units of the monomeric moiety:

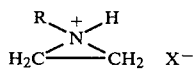

where n is a cardinal number which is proportional to the molecular weight of the polymer, R is a $C_1-C_{20}$ alkyl group, and X is a cosmetically acceptable anion such as a halide, sulfate or carboxylate.

In many of the foregoing cationic polymers quaternization can be carried out subsequent to polymerization in a manner known per se.

In the foregoing enumeration of specific cationic polymers, whether or not they also are cationic polymer products, the chemical structures are those that were given by the respective manufacturers or were otherwise postulated. Therefore the formulae dot not necessarily accurately represent the actual structures of the respective monomeric units that constitute the particular cationic polymer. For example, it was recently learned that the manufacturers of two of the cationic polymer products in the foregoing listing changed their views about the formulae which they initially provided for their respective cationic polymers without changing their respective products. The new structural representations, as provided by their respective manufacturers, appear in this application with respect to those two cationic polymer products. It is for that reason that we do not wish to be bound to any specific structural representation of any cationic polymer product herein, but in each case view the manufacturer's trademark, the CTFA designation and any chemical name (the latter usually based on what was done to a precursor to obtain the end product), to be of equal significance in defining each cationic polymer product.

All of the aforementioned cationic polymer products, which by definition of that term, will work in accordance with the present invention were determined to have a value between 3 and 5 on the combability test described above and conducted after 3 shampooings subsequent to the application of the composition. Thus their ability has been established to impart durable conditioning properties to compositions and to hair treated thereby.

Since it has been demonstrated that the functioning of the cationic polymer in accordance with the durable conditioning features of the present invention cannot be predicted, and since it has also been demonstrated how the suitability of a polymer within the above-identified group can be established by simple routine experimentation, therefore, the term "cationic polymer product", as used throughout the specification and the claims, includes all cationic polymers of the type defined above. Thus the term "cationic polymer product", as used throughout the specification and the claims, includes in its definition not only cationic polymers which have been specifically enumerated herein, but also any and all other cationic polymers which are a "cationic polymer product", as defined hereinabove, as the present invention does not reside in the identity of any given cationic polymer product, nor does it reside only in the employment of any given cationic polymer product, but in the manner that any cationic polymer product is employed.

As it can be readily appreciated, the term "cationic polymer product" is not restricted to homopolymers, but copolymers of multiple monomers are intended to be included in the meaning of the term.

Those specific cationic polymers that were enumerated above as being cationic polymer products, were found to perform, with one exception over a wide range of molecular weights between about 4,000 to about 550,000; most of them suitably from about 20,000 to about 100,000. The only exception that was found so far is Onamer which provides an effective cationic polymer product at a molecular weight between about 1,000 and about 3,000. The manner of determining and expressing the molecular weight makes no difference in this case.

The term "cationic polymer product" as used throughout the specification and the claims also includes mixtures of one or more cationic polymer products. As employed in accordance with the present invention cationic polymer product was found to be sufficient to be present in the composition between about 0.1% to about 10%, suitable from about 1% to about 5%.

The mechanism of the durable conditioning reaction obtained in accordance with the present invention is not clearly understood. We believe that initially the positively charged sites of the cationic polymer product component of the composition forms a bond with the negatively charged sites of the hair. Up to this point the assumed mechanism is similar to the known, normal conditioning of hair when positively charged monomeric or polymeric quaternary amines are employed for conditioning. While we postulate that, in accordance with our invention, the remaining free positive charges of the cationic polymer product react in the presence of hair with the anionic surfactant to form the durable conditioning complex on the hair which remains attached to the hair and conditions it through several shampoos without need for reapplication each time, we do not wish to be bound by this speculative assertion.

It was found, surprisingly, that in most cases durable conditioning could be obtained at most pH levels. Hair is built of amino acids. There are basic molecular units which contain both positive and anionic charges. When the final polymeric character of the hair is established, there is generally believed to be an equal number of the negative and positive charges present in the hair. Thus hair can be termed to be an amphoteric bipolymer. The neutrality of that system, which means that there is a region of pH at which the number of positive charges and the number of negative charges are equal, is called an isoelectric region. That isoelectric region in hair is approximately pH 4. Above pH 4, on the basis of the charges present in the hair, any agent, such as moistening the hair, should render the hair negatively charged. An agent at a pH below 4 should render the hair positively charged. While this is a theoretical dividing line in practice we find that, possibly due to the wearing properties of the hair, the surface characteristics of hair do not mirror out chemical calculations, which means that the head is able to pick up cationic materials at a pH even lower than 4. It could only pick up cationic materials if the hair surface was negatively charged; that probably can extend down to about pH 2. We can measure this activity of the cationic material by treating the hair with radioactively tagged cationic surfactants and measure the radioactivity of hair. When this is done it is found that hair has approximately no charge in terms of its surface activity or surface affinity, at about pH 2. Any cationic polymer product above pH 2 is likely to be attached to hair, although more of the surfactants are expected subsequently to be bound at pH 7 than at pH 4. Furthermore, if an amphoteric surfactant is employed, then it should be used at basic pH at which it becomes anionic.

The present invention can be carried out by first moistening the hair with an optional pre-wrap lotion. The pre-wrap lotion can be water alone, or suitably can also contain a cationic polymer product in solution. This wetting of the hair facilitates its winding around the curling rod. Suitably the pre-wrap lotion contains about 0.5% of a cationic polymer product such as the polymer being added in the form of its aqueous solution. The lotion can contain other ingredients, such as buffer, color, fragrance and preservative.

Subsequently an individual hair strand is separated from the rest of the hair on the head. A sheet of a somewhat absorbent paper, usually referred to as an "end paper" can be suitably folded over the strand of hair at or near the hair ends to facilitate wrapping; and then the strand is wound up onto a curling rod. After the hair is wound up, it is saturated with the reducing composition. The reducing lotion usually contains one or more reducers in a concentration between about 0.5% and about 20%, suitably between about 10% and 20%, and in accordance with this invention an anionic surfactant in a concentration of 0.2% to about 50%, suitably from about 0.5% to about 20%, as well as other optional ingredients such as a clarifier, wetting agent, swelling agent to make hair more receptive to the treatment, buffer, color and fragrance. Usually the reducing lotion is left on the hair for a controlled period of time at body temperature. This is usually carried out by draping a plastic cap over the saturated tresses for the desired duration.

In accordance with the present invention an amphoteric or anionic detergent constitutes part of the reducing lotion. All amphoteric detergents that have been tested were suitable for use in the present invention. Two classes of amphoteric detergents have been found to be particularly suitable. The first class can be defined by the formula:

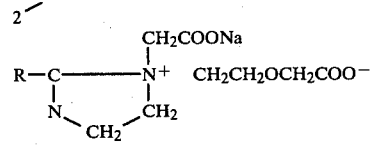

in which R is a long chain fatty radical containing from 10 to 18 carbon atoms. A typical example of such a compound or compounds is the case in which R represents coconut fatty radicals. A material of this character is sold under the trade name MIRANOL C2MSF by the Miranol Chemical Company, Inc., with its CTFA name being amphoteric-2.

A second class of amphoteric detergents that is particularly effective for the purpose of the present invention can be defined by the formula:

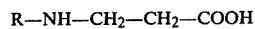

wherein R is a long chain fatty alkyl group having from 10 to 18 carbon atoms. An example of such a detergent is marketed under the trade name DERIPHAT 170C by General Mills Chemicals, Inc., with its CTFA name being lauraminopropionic acid in which the R is a mixture of lauryl and myristyl fatty alkyl groups.

All anionic surfactants tested have been found useful in this invention; thus, salts of alkyl sufonates, alkyl sulfates, sulfonated and sulfated alkyl ethers as well as long chain carboxylic acid (where the chain length is constituted of at least 10 carbon atoms) exhibit formation of durable conditioning complexes. By way of specifically illustrating suitable anionic detergents we mention sodium lauryl sulfate, sodium lauryl ether sulfate, TEA lauryl sulfate, sodium stearate, etc.

The quantity of amphoteric or anionic detergent which will be contained in the reducing lotion of this invention will vary somewhat depending on the economics and the results sought. However, usually this will be in the range of from about 0.2% to about 50% and suitably in the range of from about 0.5% to about 20%.

After the required reduction time, the wound up tresses are usually rinsed with water and the hair is saturated with the neutralizing lotion. The neutralization step generally involves the use of a neutralizing lotion which contains from about 0.2% to about 20%, suitably from about 1% to about 8%, of an oxidizer and a buffer suitably to adjust it to a preferably acidic pH, most suitably at about pH 3–4. Hair is also effectively de-swelled at that pH, which also assists in restoring the keratin linkages.

In accordance with the present invention the neutralizing solution can optionally also contain a cationic polymer product whether or not the pre-wrap lotion also contained such a polymer in solution. If the pre-wrap solution did not contain a cationic polymer product, then it is required in accordance with the present invention that it be included in the neutralizing solution. The concentration of the cationic polymer product in the neutralizing solution can be conveniently high, such as up to even 25%, to make certain that all of the unreacted anionic surfactant which remained in the hair after rinsing, is now reacted with the cationic polymer product in the neutralizing lotion. It is our belief that the over-conditioning of hair or the depositing on, and bonding to, hair of excessive amounts of the conditioning complex, is avoided in the use of the present invention. We believe that this is because the number of negative charges on hair, which can accept a conditioning deposit, is proportional to the need and locations on the hair that require conditioning. Therefore, we would expect that any excess of detergent, cationic polymer product or complex formed by them, would rinse away rather than deposit onto and overcondition the hair.

Of course, if an amphoteric surfactant was used in the reducing lotion, and the particular waving or straightening system requires neutralization at an acidic pH, below the $pk_a$ value of the amphoteric, then it is essential that a cationic polymer product be used in the pre-wrap lotion, because under the effect of that acid pH in the neutralizing lotion the amphoteric surfactant will become cationic and it will not react with a cationic polymer product. This consideration does not apply if neutralization is carried out at basic pH.

EXAMPLES

A number of experiments are carried out by using unbleached, intact female Caucasian hair. Throughout the specification and the claims all percentages are by weight, based on the particular solution in which the ingredient is contained.

In all examples the following conventional base compositions are employed (all names are either CTFA names or chemical nomenclature):

| Pre-Wrap Base Solution: | | |
|---|---|---|
| DMDM hydantoin | 0.4% | (preservative) |
| laureth-23 | 2.0% | (wetting agent) |
| D & C yellow | 0.02% | |
| buffer to pH 9 | 0.02% | |
| water to | 100 | |

| Reducing Base Lotion: | | |
|---|---|---|
| ammonium thioglycollate | 7.0% | |
| monoethanolamine | 3.5% | |
| fragance | 0.1% | |
| ammonium lauryl sulfate | 8.5% | (anionic surfactant according to the invention) |
| water to | 100 | |

| Neutralizing Base Lotion: | | |
|---|---|---|
| hydrogen peroxide | 4.5% | |
| sodium citrate | 0.6% | (buffer to pH 3) |
| water to | 100 | |

In all of the following examples the hair tresses are wound onto ½" diameter rods. In each example the relative conditioning value is determined after 3 subsequent shampooings. The tabular representation of the examples indicates the identity and concentration, if any, of the cationic polymer product that is included in the aforementioned base composition. In the examples the resting of the hair saturated with the reducing solution on the live head is substituted by wrapping the tresses in Saran plastic webbing and holding at 35° C.

| Example | Pre-wrap | Neutralization | Conditioning Rating |
|---|---|---|---|
| 1 | quaternium-40 1% | — | 5 |
| 2 | — | quaternium-40 4% | 5 |
| 3 | onamer 1% | quaternium-40 4% | 5 |
| 4 | onamer 1% | — | 4 |
| 5 | — | onamer 4% | 4 |
| 6 | QPVP 1% | — | 5 |
| 7 | — | QPVP 4% | 5 |
| 8 | Clairquat-1 1% | — | 5 |
| 9 | Clairquat-1 1% | Clairquat-1 4% | 5 |
| 10 | — | Clairquat-1 4% | 5 |
| 11 | QPVAMINE 1% | — | 3 |
| 12 | onamer 1% | QPVAMINE 4% | 4 |
| 13 | QPEMINE 1% | — | 4 |
| 14 | — | QPEMINE 4% | 4 |

A control tress which is not treated in accordance with the present invention provides a conditioning rating of 1, after soaking in water.

Another control tress is treated in accordance with the disclosure of U.S. Pat. No. 3,912,808, by exposure to a reducing lotion similar to the base composition used herein, except that the ammonium lauryl sulfate in the reducing lotion base composition is replaced by 1.5% quaternium-40. The air is subsequently throroughly rinsed, then is neutralized with the neutralizing base composition and then is thoroughly rinsed twice more. The resulting tress has a conditioning rating of 2.

Although the invention was described with reference to specific examples thereof, it will be understood that many changes and modifications can be made without departing from the spirit of the invention which is defined by the claims hereof.

We claim:
1. In a process for waving or straightening hair, which comprises the sequential steps of:
   (a) moistening the hair with an aqueous solution;
   (b) winding strands of the hair over curling rods;
   (c) contacting the hair with a composition which contains a reducing agent;
   (d) rinsing the hair;
   (e) contacting the rinsed hair with a composition which contains a neutralizing agent;
the improvement which comprises:
   (i) said composition employed in step (a) containing at least one cationic polymer product which forms a substantially water insoluble complex with an anionic surfactant in the presence of hair; and
   (ii) said composition employed in step (c) containing at least one anionic surfactant.

2. In a process for waving or straightening hair, which comprises the sequential steps of:
   (a) moistening the hair with an aqueous solution;
   (b) winding strands of the hair over curling rods;
   (c) contacting the hair with a composition which contains a reducing agent;
   (d) rinsing the hair;
   (e) contacting the rinsed hair with a composition which contains a neutralizing agent;
the improvement which comprises:
   (i) said composition employed in step (a) containing at least one cationic polymer product which forms a substantially water insoluble complex with an anionic surfactant in the presence of hair;
   (ii) said composition employed in step (c) containing at least one anionic surfactant; and
   (iii) the composition employed in step (d) or the composition employed in step (e) containing at least one cationic polymer product which can be the same or different from the cationic polymer product employed in step (a).

3. The process of claim 1 or 2, wherein said cationic polymer product is a cationic polymer which has at least one positively charged nitrogen or sulfur moiety in each periodically repeating unit.

4. The process of claim 3, wherein said cationic polymer product is a homo or copolymer containing a secondary, tertiary or quaternary nitrogen group in each periodically repeating unit.

5. The process of claim 1 or 2, wherein said step (ii) is carried out before, after or both before and after said step (a), and if said step (ii) is carried out both before and after said step (a), then the cationic polymer product can be the same or different on each of the two occasions.

6. The process of claims 1 or 2, wherein the improvement in the composition employed in said step (c) comprises from about 0.2% to about 50% of said anionic surfactant, and wherein the composition employed in said step (i) comprises from about 0.1% to about 25% of the cationic polymer product.

7. The process of claims 1 or 2, wherein the improvement in the composition employed in said step (c) comprises from about 0.5% to about 20% of said anionic surfactant, and wherein the composition employed in said step (i) comprises from about 1% to about 5% of the cationic polymer product.

8. The process, which comprises the steps of:
   (I) moistening the hair to be waved or straightened with an aqueous solution containing from about 0.1% to about 10% of a cationic polymer product in solution;
   (II) wrapping the hair onto waving or straightening rods;
   (III) substantially saturating the hair with an aqueous solution containing a reducing agent and from about 0.2% to about 50% of an anionic surfactant;
   (IV) resting substantially saturated hair for a predetermined period;
   (V) rinsing the hair with water;
   (VI) substantially saturating the hair with a composition containing a neutralizing agent; and
   (VII) removing the hair from said rods.

9. The process of claim 8, wherein the composition employed in said step (VI) further contains from about 0.1% to about 25% of a cationic polymer product in solution.

10. The process which comprises the steps of:
   (I) substantially saturating hair with a composition containing a reducing agent and from about 0.2% to about 50% of an anionic surfactant;
   (II) substantially washing out said composition employed in step (I) from the hair; and
   (III) substantially saturating the hair with a composition containing a neutralizing agent and from about 0.1% to about 25% of a cationic polymer product in solution.

11. The process of any of the preceding claim 1, 2, 8 or 10 wherein said cationic polymer product is in aqueous solution.

12. The process of any of the preceding claim 1, 2, 8 or 10 wherein the cationic polymer product is in aqueous solution and comprises quaternium-40.

13. The process of any of the preceding claim 1, 2, 8 or 10 wherein the cationic polymer product is in aqueous solution and comprises Onamer.

14. The process of any of the preceding claim 1, 2, 8 or 10 wherein the cationic polymer product is in aqueous solution and compries QPVP.

15. The process of claim 14 wherein the cationic polymer product is a QPVP halide.

16. The process of any of the preceding claim 1, 2, 8 or 10 wherein the cationic polymer product is in aqueous solution and comprises Clairquat-1.

17. The process of any of the preceding claim 1, 2, 8 or 10 wherein the cationic polymer product is in aqueous solution and comprises QPVAMINE.

18. The process of any of the preceding claim 1, 2, 8 or 10 wherein the cationic polymer product is in aqueous solution and comprises QPEMINE.

19. The process of any of the foregoing claim 1, 2, 8 or 10 wherein said reducing agent is at least one of a mercaptyl carboxylic acid, an ester or a salt thereof; an alkali salt of a sulfurous acid; cysteine; guanidine or a salt thereof; and tris (hydroxyethyl) phosphine.

20. The process of any of the foregoing claim 1, 2, 8 or 10 wherein the neutralizing agent is an oxidant.

21. The process of claim 20, wherein the oxidant is a peroxide or a bromate.

22. A package containing a plurality of containers which comprise compositions to be employed in a process for waving or straightening of hair, a first one of said containers containing a composition comprising a reducing agent and between about 0.2% and about 50% of an anionic surfactant, and second one of said containers containing a composition comprising between about 0.1% and 0.25% of a cationic polymer product, and a neutralizing agent which is in a third container or in said second container together with said cationic polymer product.

23. The package of claim 22, wherein the concentration of the anionic surfactant in said first container is between 0.5% and 20%, and wherein the concentration of the cationic polymer product is between 1% and 5%.

24. The package of claims 22-23, wherein the neutralizing agent is contained in said second container together with said cationic polymer product and the package further containing a third container containing an aqueous solution of a cationic polymer product.

25. The package of claims 22-23, wherein the package further contains instructions on how to employ the contents of the containers for waving and straightening hair.

* * * * *